United States Patent [19]

Rieser

[11] Patent Number: 5,437,661
[45] Date of Patent: Aug. 1, 1995

[54] METHOD FOR REMOVAL OF PROLAPSED NUCLEUS PULPOSUS MATERIAL ON AN INTERVERTEBRAL DISC USING A LASER

[76] Inventor: Bernhard Rieser, Simmler Str. 4, 75172 Pforzheim, Germany

[21] Appl. No.: 216,300
[22] Filed: Mar. 23, 1994
[51] Int. Cl.⁶ .............................................. A61B 17/36
[52] U.S. Cl. ...................................... 606/15; 606/16; 609/164
[58] Field of Search ................................ 606/3, 13–19; 604/164

[56] References Cited

U.S. PATENT DOCUMENTS

| | | |
|---|---|---|
| 4,545,374 | 10/1985 | Jacobson . |
| 4,772,266 | 9/1988 | Groshong ............................ 604/164 |
| 4,959,063 | 9/1990 | Kojima ................................. 606/15 |
| 5,084,043 | 1/1992 | Hertzmann .......................... 606/3 |
| 5,120,318 | 6/1992 | Mononen et al. .................... 604/164 |
| 5,131,382 | 7/1992 | Meyer . |
| 5,158,543 | 10/1992 | Lazarus ................................ 604/164 |
| 5,285,795 | 2/1994 | Ryan et al. .......................... 606/16 X |
| 5,290,279 | 3/1994 | Bonati et al. ....................... 606/16 X |

Primary Examiner—Peter A. Aschenbrenner
Attorney, Agent, or Firm—Lott & Friedland

[57] ABSTRACT

A method for removal of prolapsed nucleus pulposus material of an intervertebral disc of a patient using a laser is disclosed. The present invention provides applying a laser beam directly in contact with the prolapsed nucleus pulposus material within the spinal foramen of an intervertebral disc, whereby the laser beam eliminates the prolapsed nucleus pulposus material, without touching the intervertebral disc. A cannula is inserted into the spinal foramen. Once the cannula has passed the ligamentum flavum, a laser fiber is inserted into the cannula. The laser fiber contacts the prolapsed material and a laser beam substantially eliminates the prolapsed material within the spinal foramen.

11 Claims, 10 Drawing Sheets

METHOD FOR REMOVAL OF PROLAPSED NUCLEUS PULPOSUS MATERIAL ON AN INTERVERTEBRAL DISC USING A LASER

TECHNICAL FIELD

This invention relates generally to a method for removal of prolapsed nucleus pulposus material of an intervertebral disc, and this invention specifically relates to a method for removal of prolapsed nucleus pulposus material within the spinal foramen of an intervertebral disc using a laser to eliminate the prolapsed material.

BACKGROUND OF THE INVENTION

According to U.S. News and World Report, about 300,000 of the 10 million Americans who hurt their backs each year wind up on the operating table. Most of the operations are for ruptured discs, the rubbery, shock-absorbing cushions between the bones of the spine. Among humans, herniated discs are a common cause of back trouble. According to the National Center for Health Statistics' (NCHS) Health Interview Survey, there are more than two and a half million men and women in the United States with displaced discs, half of them with trouble severe enough that they saw a doctor or had to limit their activities.

Figures 1, 2, 3, 4:
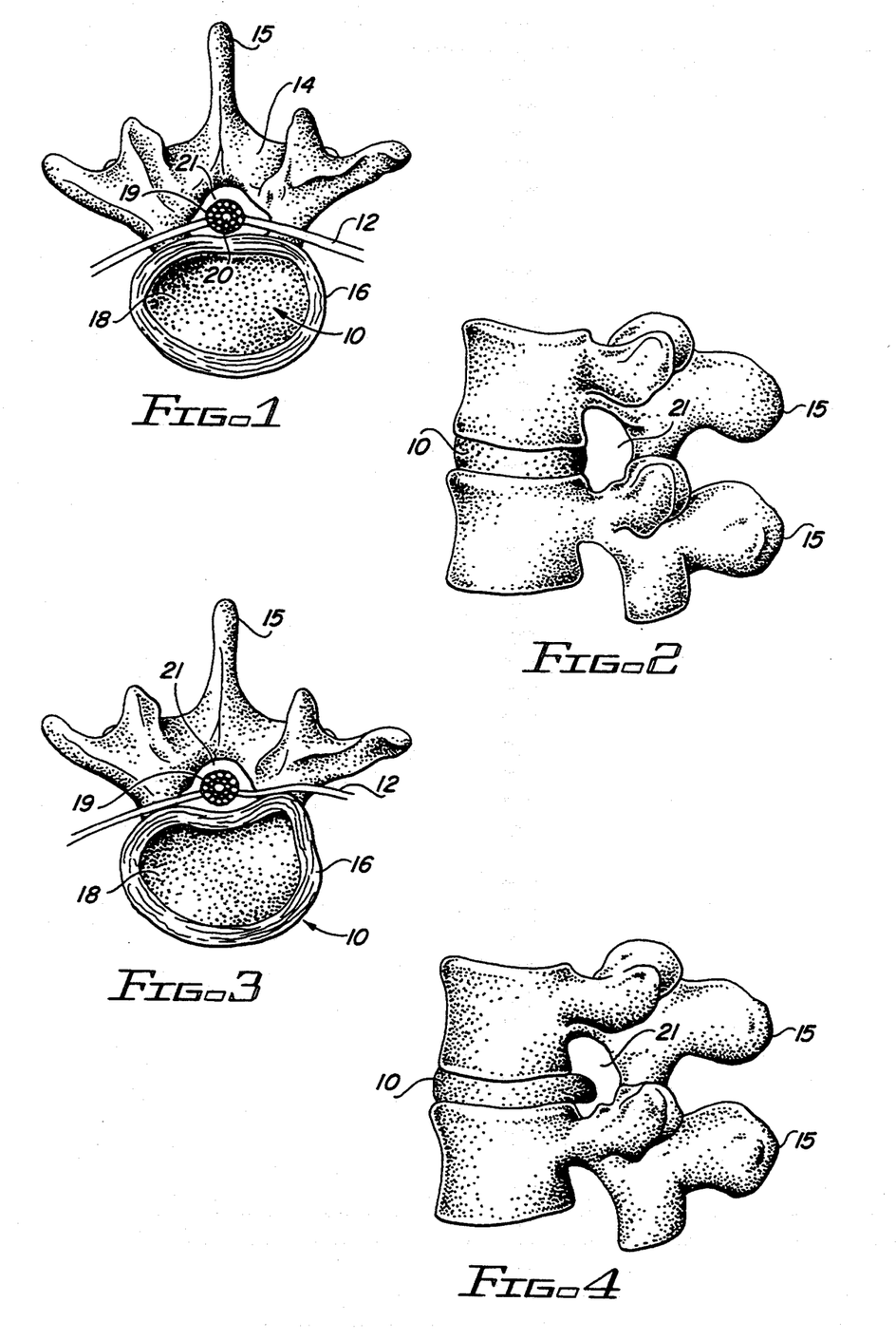
FIG. 1 is a sectional view of a normal lumbar disc, nerve root and inferior vertebrae.
FIG. 2 is an oblique view of the normal lumbar disc and inferior vertebrae of FIG. 1.
FIG. 3 is a sectional view of a herniated lumbar disc, nerve root and inferior vertebrae.
FIG. 4 is an oblique view of the herniated lumbar disc and inferior vertebrae of FIG. 3.

Shooting pains down the leg, called sciatica, that persist for six weeks or so probably mean that the gelatinuos material inside the disc, the nucleus pulposus, has leaked through the fibrous outer portion, the annulus fibrosus, forming a hernia which is pressing on a nerve. Though the popular misnomer for this condition is a "slipped disc", there is, in fact, no slippage. Instead, the affected disc balloons out from between the bony parts of the vertebrae. FIGS. 1 and 2 illustrate a normal disc, while FIGS. 2 and 3 show a herniated disc. Herniation most frequently affects the forth and fifth discs in the lumbar region although this problem can also occur in the uppermost vertebrae (cervical) around the neck.

If the ruptured disc presses on a nerve root in such a way to cause muscular weakness or interference with bladder function, most physicians recommend immediate surgery to remove the disc and thus relieve the pressure on the nerve. Such surgery is called a diskectomy (literally, removal of a disc) or sometimes a laminectomy, because surgeons usually cut through the lamina of a vertebra (the portion between the spinous and transverse process) to get at the disc.

In a laminectomy, access to the nucleus is made by cutting a channel from the rear of the patient's back through the vertebral lamina to the disc. Because of this cutting, a laminectomy is a very destructive process, which often leads to permanent scarring with more pain than the original prolapsed disc. Another disadvantage is that laminectomies often require long hospitalization and postoperative recovery periods, typically from one to two months, if there have been no complications.

Back surgery candidates naturally want the least invasive form of disc surgery. A patient with a contained disc herniation (FIGS. 3 and 4) might be referred for discectomy, microdiscectomy, (automated or manual) percutaneous discectomy, arthroscopic discectomy, laser-assisted disc decompression (LDD), or chemonucleolysis. One major disadvantage of all of these less-invasive disc procedures is that they are limited to contained herniations, which are protrusions in which disc material has not broken through the annulus.

Chemonucleolysis was the first of the less invasive surgical techniques used to treat contained disc herniations. In 1982, the Food and Drug Administration approved this drug treatment. The drug, chymopapain, is injected into the central portion, the nucleus pulposus, of the diseased disc to dissolve some of the disc substance in an attempt to relieve pressure against a nerve or other soft tissue.

One major disadvantage associated with the use of chymopapain is that one out of every one hundred people can suffer a severe allergic reaction called anaphylaxis. Occasionally, this allergic reaction is fatal.

A further disadvantage is that if severe or moderate pain persists, with or without nerve root pressure, and chemonucleolysis either failed or was not deemed advisable by a surgeon, an operation will still be necessary.

Another known procedure is a microsurgical diskectomy (microdisectomy), a similar technique to arthroscopic knee surgery. As in laminectomy, the disc is accessed by cutting a channel from the rear of the patient's back to the disc, but the microscope permits the surgeon to operate through a smaller incision—typically 1 to 1.5 inches, compared with about 2.4 inches for conventional discectomy. With the use of an operating microscope, smaller diameter microsurgical instruments can pass through the vertebral laminae without bone cutting. Although microsurgical diskectomy has fewer complications and shorter hospital stay than laminectomy, blood vessels and nerves are still retracted, and scarring and post operative pain is not eliminated.

Another disadvantage of microdiscectomy is that it because of the small incision, surgeons may find themselves exploring the wrong spinal level, missing pathology that is outside of the limited operating field, or damaging neural structures. Additionally, if hemorrhaging is not controlled, the surgeon's view of the operating field can be severely compromised. Infection is another worry, as it is difficult to completely sterilize the operating microscope.

It has been stressed that this type of disc surgery is most effective only in younger individuals who have so-called "soft herniations"—i.e. when the nerve root compression is caused solely by protruding soft tissue, also known as "contained herniations". Noncontained herniations, or sequestered discs, in which disc fragments have migrated beyond the border of the annulus, are not accessible with this approach.

Percutaneous diskectomy is an alternative minimal-surgery procedure developed for treatment of herniated discs. The procedure is done with either manual instruments, such as pituitary rongeurs, or an automated suction aspiration probe called the nucleotome. The procedure consists of placing a long-bore needle through the back muscles on one side of the spine right into the center of the disc. A tiny blade is passed through the needle into the center of the disc, and this cutting blade is used to mince the inner disc tissues. This material is then asperated out of the body by suction through an inner tube within the needle. The result is a creation of a hole within the disc similar to that which occurs when the disc is dissolved by chemonucleolysis. The bulging disc material can then collapse back in toward the center of the disc. This "debulking" of the disc theoretically reduces pressure on the adjacent spinal nerves, relieving symptoms.

An example of manual percutaneous discectomy is illustrated in U.S. Pat. No. 4,545,374 to Jacobson, incorporated herein by reference. Jacobson generally describes a method and instruments for performing a percutaneous lumbar disectomy. In order to remove disc nucleus material, a cannula is passed laterally through the body. Disc removal instruments are then passed through the cannula to the disc. To help the surgeon visually monitor the area around the injured disc and prevent improper positioning of the instruments, fluoroscopic X-ray may be used.

One major disadvantage associated with the percutaneous diskectomy procedure, like that described in Jacobson, is that percutaneous discectomy only removes material from the center of the disc. It does not allow the surgeon to excise fragments that had migrated toward the back and sides. Although these fragments sometimes retract when nuclear material is removed from the center, they will often migrate to the periphery of the disc. If left in place, the fragments can cause recurrent radicular symptoms.

Another disadvantage is that noncontained herniations, or sequestered herniations are unsuitable for this technique. The originator of the automated percutaneous discectomy, Gary Onik, M.D. recommends using this procedure in herniations that are localized in front of the intervertebral space and have not broken through the annulus.

Laser-assisted disc decompression (LDD) is another technique to reduce the amount of hydraulic pressure inside of a contained herniated disc. In LDD, the surgeon vaporizes the disc nucleus material to relieve pressure.

An example of this method of surgery is illustrated in U.S. Pat. No. 5,084,043 to Hertzmann et al., incorporated herein by reference. Hertzmann generally describes a method for performing percutaneous diskectomy using a laser to vaporize material in the nucleus pulposus. Conventionally, a computed tomograph (CT) scan slice of the whole abdomen through the involved disc is used to help determine the entry path.

A disadvantage of all of these less-invasive procedures is that when the bulge has actually broken through the annulus fibrosis (noncontained hernia or prolapse), the bulging disc material may be prevented from collapsing back in toward the center of the disc. Thus, removal of disc material from the nucleus pulposus will not remove the bulge which is causing the painful pressure on nerves.

One possible solution to these problems is to provide a less-invasive procedure which actually removes the bulge or prolapse itself for noncontained herniated discs within the spinal foramen.

Another possible solution to these problems is to provide a procedure which does not involve operating on the nonherniated portion of the nucleus pulposus.

Another possible solution to these problems is to provide a procedure which does not involve chemical side effects or allergic reactions.

Another possible solution is to provide a procedure which requires a minimal hospitalization period and post-operative recovery time.

A further solution to these problems is to provide a procedure in which the surgeon can visually monitor the procedure though a specially designed optical system.

Thus, there is a need in the art for a less-invasive procedure which actually removes the bulge or prolapse itself for noncontained herniated discs within the spinal foramen and which does not involve operating on the nonherniated portion of the nucleus pulposus.

There is an additional need in the art for a procedure which does not involve chemical side effects or allergic reactions and requires only a minimal hospitalization period and post-operative recovery time.

There is an additional need in the art for a procedure in which the surgeon can visually monitor the procedure though a specially designed optical system.

SUMMARY OF THE INVENTION

The present invention solves significant problems in the art by providing a method for removal of prolapsed nucleus pulposus material within a spinal foramen of an intervertebral disc of a patient using a laser, comprising applying a laser beam directly in contact with the prolapsed nucleus pulposus material, whereby the laser beam eliminates the prolapsed nucleus pulposus material.

Generally described, the method comprises removal of prolapsed nucleus pulposus material within a spinal foramen of an intervertebral disc of a patient using a laser.

In a preferred embodiment of the present invention, the method for removal of prolapsed nucleus pulposus material within a spinal foramen of an intervertebral disc of a patient using a laser, comprises applying a laser beam directly in contact with the prolapsed nucleus pulposus material, whereby the laser beam eliminates the prolapsed nucleus pulposus material.

The step of applying the laser beam comprises the steps of puncturing the patient's skin at an entry point with a leading wire; inserting the leading wire into the spinal foramen up to the nucleus pulposus material along an entry path, whereby the entry path passes through a section of ligamentum flavum alongside the dural sac; inserting a cannula over the leading wire into the spinal foramen; removing the leading wire from the cannula; inserting into the cannula, in place of the leading wire, a laser fiber; touching the prolapsed nucleus pulposus material with the laser fiber; applying a laser beam to the prolapsed nucleus pulposus material with the laser fiber, whereby the prolapsed nucleus pulposus material is thereafter substantially eliminated.

In an alternate embodiment of the invention, the step of inserting a cannula into the spinal foramen comprises the steps of inserting a blunt tipped dilatator and the cannula over the leading wire down to the ligamentum flavum, wherein the dilatator is located between the leading wire and the cannula; replacing the dilatator with a sharp tipped trepan; drilling a hole through the ligamentum flavum; replacing the trepan with the dilatator; passing the cannula and the dilatator through the ligamentum flavum into the spinal foramen; and removing the dilatator.

In an alternative embodiment of the invention, the method further comprises prior to the step of inserting a laser fiber, inserting an optical system into the needle portion.

In an alternative embodiment of the invention, the method further comprises prior to the step of puncturing the spinal foramen, employing a visual system throughout to allow visualization of the method. The visual system comprises a fluoroscopic X-ray system, a Computed Tomograph (CT), or a (MRI) Magnetic Resonance Imaging system.

In an alternative embodiment of the invention, the method further comprises after the step of inserting a laser fiber, inserting a free channel into the spinal foramen for suction.

In an alternative embodiment of the invention, the method further comprises after the step of inserting a laser fiber, inserting a second channel, into the spinal foramen for a peristalic pump.

In an alternative embodiment of the invention, the method further comprises after the step of passing the needle through a section of ligamentum flavum, cooling an area around the intervertebral disc, whereby the cooling extends to an associated root and a section of a spinal cord near the intervertebral disc.

In an alternative embodiment of the invention, the visual system, includes a computer of a Computed Tomograph (CT) for enhanced visual monitoring.

Accordingly, it is an object of the present invention to provide a method for removal of prolapsed nucleus pulposus material within a spinal foramen of an intervertebral disc of a patient using a laser.

It is another object of the present invention to provide a less-invasive procedure which actually removes the bulge or prolapse itself for noncontained herniated discs within the spinal foramen and which does not involve operating on the nonherniated portion of the nucleus pulposus.

It is a feature of the invention to provide an optical system in which the surgeon can visually monitor the procedure.

An advantage of the invention is that it does not involve chemical side effects or allergic reactions and requires only a minimal hospitalization period and post-operative recovery time.

These and other objects, features, and advantages of the present invention may be more clearly understood and appreciated from a review of the following detailed description of the disclosed embodiments and by reference to the appended drawings and claims.

DETAILED DESCRIPTION OF THE PREFERRED EMBODIMENT

There exists various types and degrees of disc herniation. Referring initially to FIGS. 1 and 2 of the drawings, in which like numerals indicate like elements throughout the several views, a sectional view of a normal lumbar disc 10, nerve root 12 and inferior vertebrae 14 is shown. The intervertebral disc 10 consists of circular layers of fibrous ligaments which ring the rims of each vertebral body called annulus fibrosus 16. The semi-liquid center of the disc is the nucleus pulposus 18. In a normal lumbar disc 10, the disc 10 does not come into contact with the nerve root 12 extending from the spinal cord 20.

Turning now to FIGS. 3 and 4 a herniated lumbar disc 10, nerve root 12 and inferior vertebrae 14 is shown. The disc 10 shown comes in contact with the nerve root 12, and it is this pressure on the nerve 12 which may cause pain, numbness, or other problems.

Figures 5, 6, 9, 10, 11:
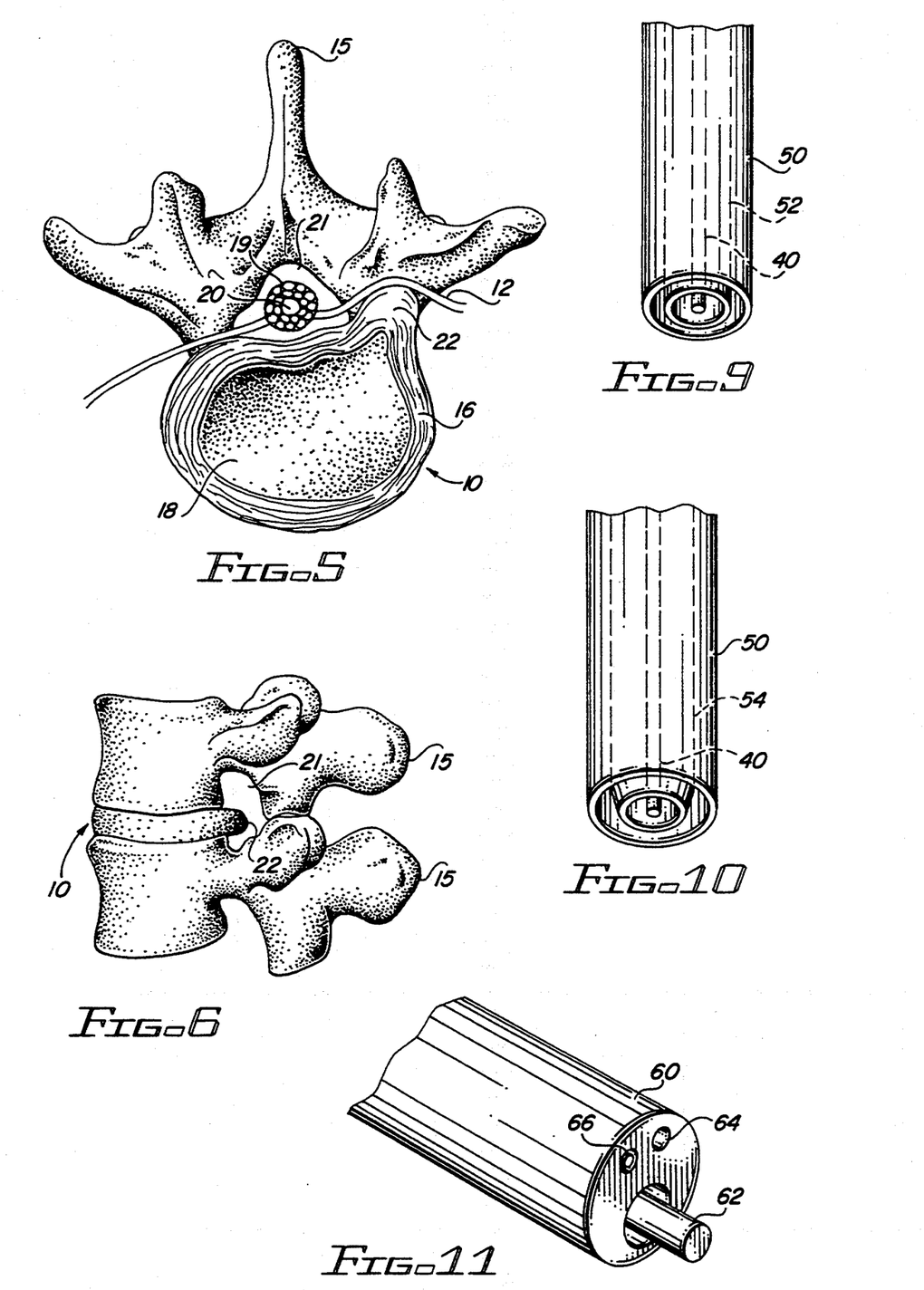
FIG. 5 is a sectional view of a non-contained herniated lumbar disc with torn annulus fibrosis, also known as a prolapse, the associated pinched nerve root and inferior vertebrae.
FIG. 6 is an oblique view of a non-contained herniated lumbar disc with torn annulus fibrosis, also known as a prolapse, the associated pinched nerve root and inferior vertebrae.
FIG. 9 is a pictoral view representing the cannula with the dilatator and leading wire within according to the preferred embodiment of the invention.
FIG. 10 is a pictoral view representing the cannula with the trepan and leading wire within according to the preferred embodiment of the invention.
FIG. 11 is a pictoral view representing optical system according to the preferred embodiment of the invention.

FIG. 5 is a sectional view of a non-contained herniated lumbar disc 10 with torn annulus fibrosis 16, the associated pinched nerve root 12 and inferior vertebrae 14. FIG. 6 is an oblique view of a non-contained herniated lumbar disc 10 with torn annulus fibrosis 16. The non-contained area is also described as the prolapse material 22. These types of herniation are sequestered, transligamentaneous or large subligamentous, and usually can only be treated by open surgery. A non-contained herniation occurs when the nucleus pulposus material 22 protrudes through the torn annulus 16. This condition is described as an extruded disc and may be subligamentous or transligamentous, with the nuclear fragment 22 remaining in contact with the interior of the disc space. A sequestered disc occurs when a part of the prolapsed material 22 has separated from the disc space and has moved through the torn posterior longitudinal ligament. The sequestered material 22 lies free in the spinal canal (foramen) 21.

The procedure of the present invention of removal of prolapsed nucleus pulposus material 22 within a spinal foramen 21 of an intervertebral disc 10 of a patient using a laser 58 is designed for patients commonly showing clinically and radiologic evidence of nerve root 12 impingement. After being diagnosed as having a prolapsed disc, in a preferred surgical method, the patient is positioned on a table, such as a Computed Tomograph Table (CT-Table) in a prone or lateral decubitus position to determine the exact level of the prolapsed disc 10. The level of the prolapsed disc 10 is shown by a CT-scan, highlighted on the skin by a beam of light and then marked by hand directly onto the skin 11. The possible pathway 32 of the flexible leading wire 40, also known as a trocar, is marked in the computer of the CT, the pathway avoiding puncturing of the dural (thecal) sac 19.

Referring now to FIGS. 7A–7H and 8A–8H and 8, the distance (W) from the spinal process 15 to the pathway 32 is measured. The depth (D) from the skin 11 to the ligamentum flavum 13 is also measured. The entry point 30 is marked on the patient by projecting the measured distance (W) between the spinal process 15 to the pathway 32 on the skin of the patient. The entry point 30 is preferably between 1–8 cm from the midline of the spinal process 15 of the torn disc 10.

The area of the entry point 30 is disinfected. The point of entry 30 is then injected with local anesthesia down to the ligamentum flavum 13 by a long needle. The correct position of the needle is preferably shown by the CT.

Figure 7A:
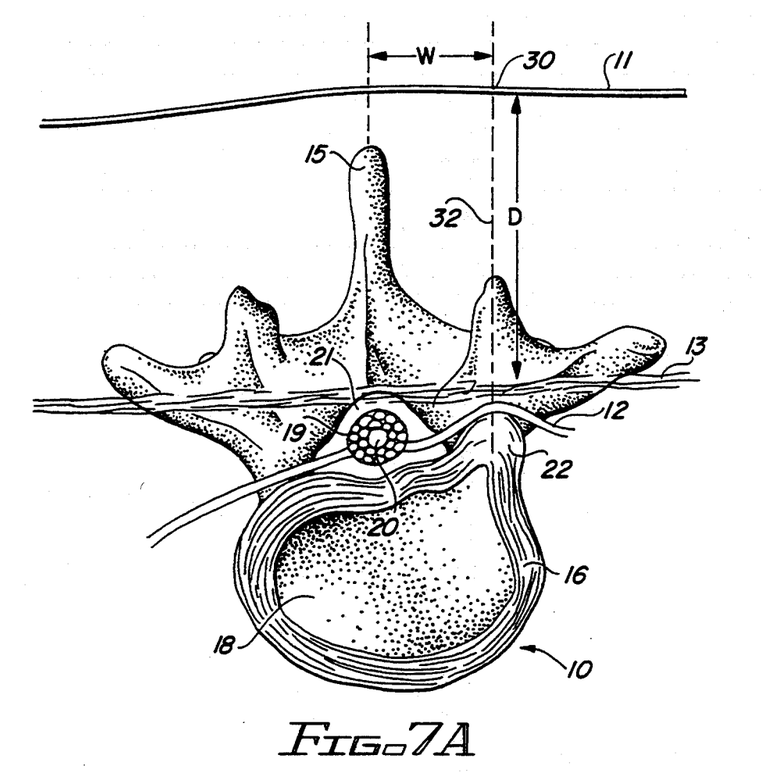
FIG. 7A is a sectional view of a non-contained herniated lumbar disc with torn annulus fibrosis, also known as a prolapse, the associated pinched nerve root and inferior vertebrae, illustrating the entry path according to the invention.
Figure 7B:
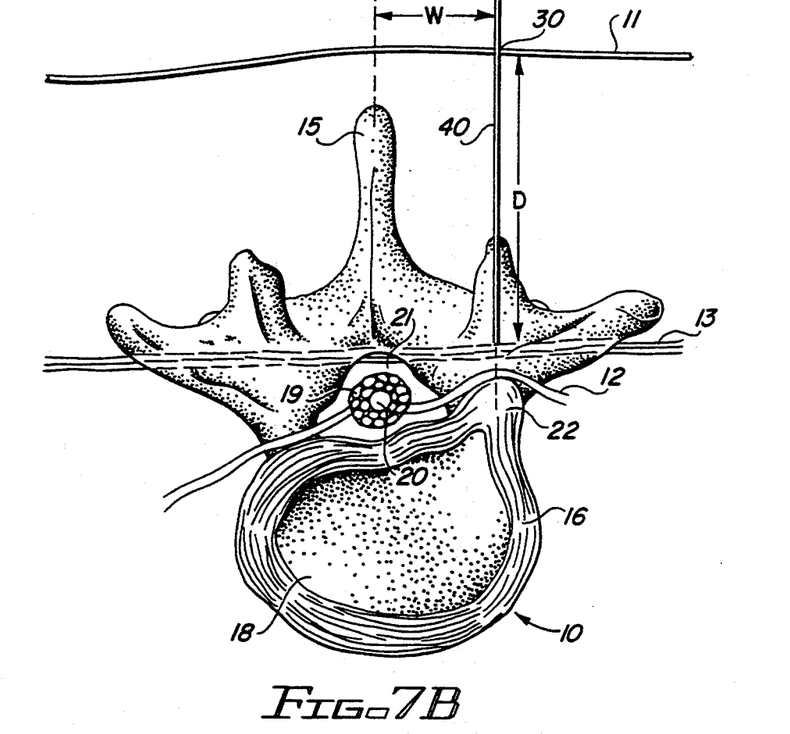
FIG. 7B is a sectional view of a non-contained herniated lumbar disc illustrating insertion of the leading wire.
Figure 8A:
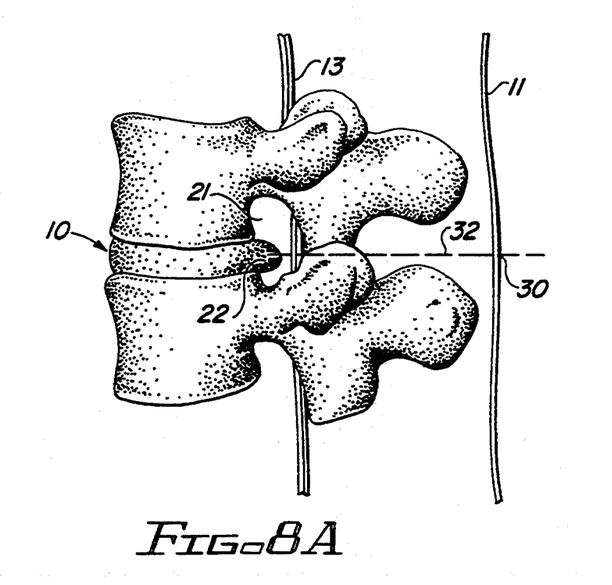
FIG. 8A is an oblique view of a non-contained herniated lumbar disc with torn annulus fibrosis, also known as a prolapse, the associated pinched nerve root and inferior vertebrae, illustrating the entry path according to the present invention.
Figure 8B:
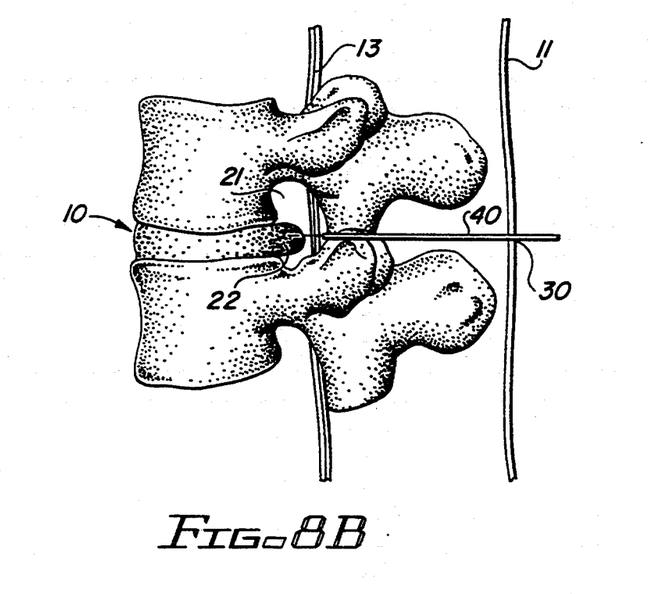
FIG. 8B is an oblique view of a non-contained herniated lumbar disc illustrating insertion of the leading wire.

A small incision is then made in the skin at the entry point 30 and the needle is replaced by the leading wire 40, FIGS. 7B and 8B, preferably with a diameter approximately 1.5 mm. As with the needle, the exact position of the leading wire 40 can be controlled by the CT. Once the leading wire 40 is in the correct position, the ligamentum flavum 13 is punctured, passing the dural sac 19, up to the prolapsed material 22. The correct final position is verified by the CT.

Figure 7C:
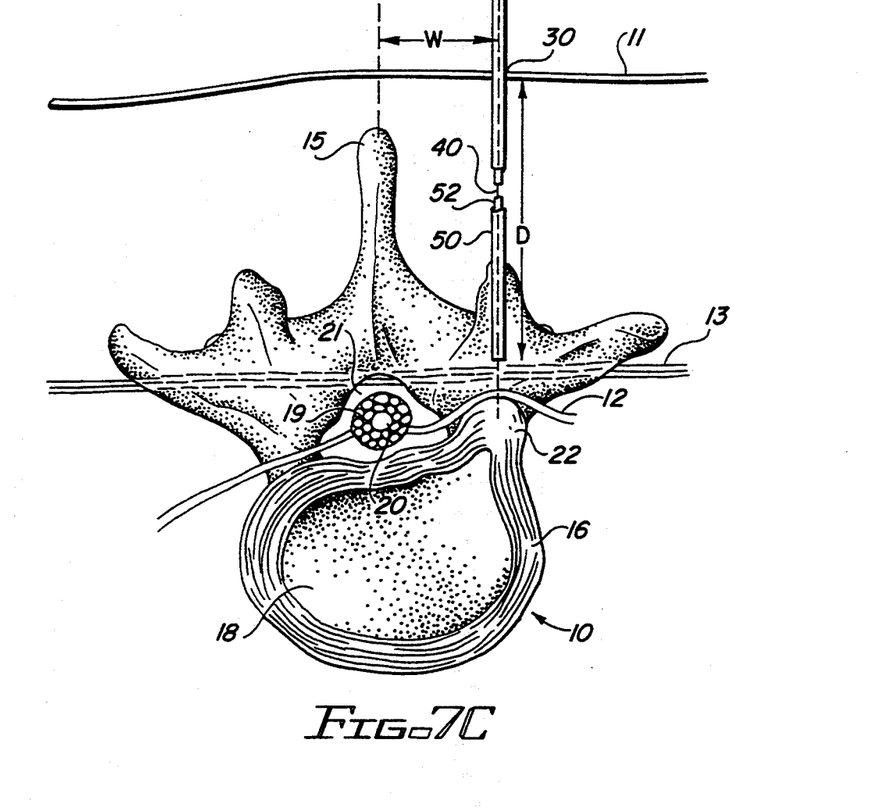
FIG. 7C is a sectional view of a non-contained herniated lumbar disc illustrating insertion of the dilatator and cannula over the leading wire.
Figure 7D:
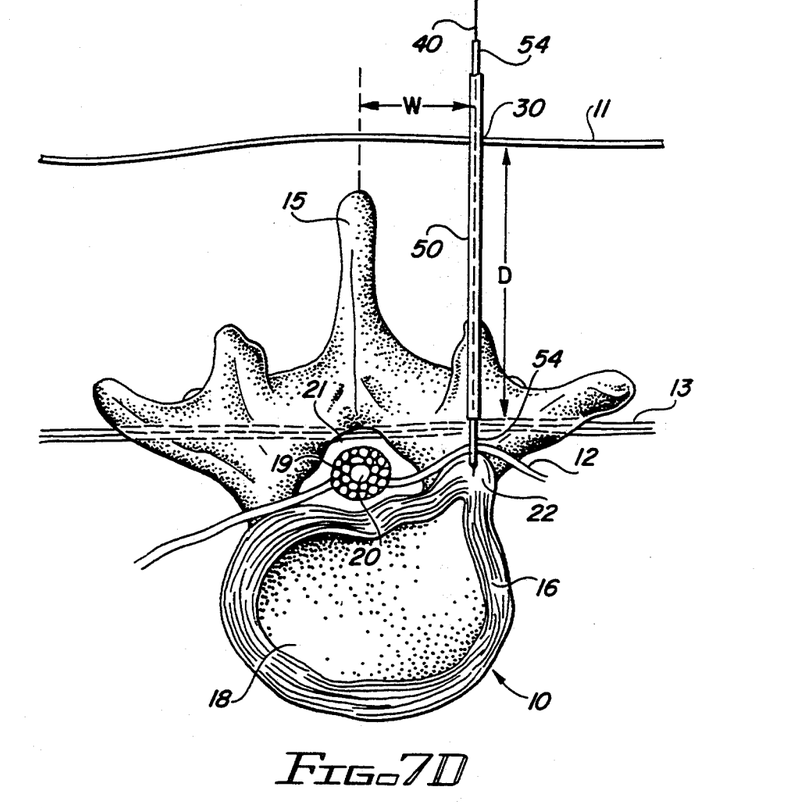
FIG. 7D is a sectional view of a non-contained herniated lumbar disc illustrating insertion of the trepan in place of the dilatator drilling through the ligamentum flavum.
Figure 7E:
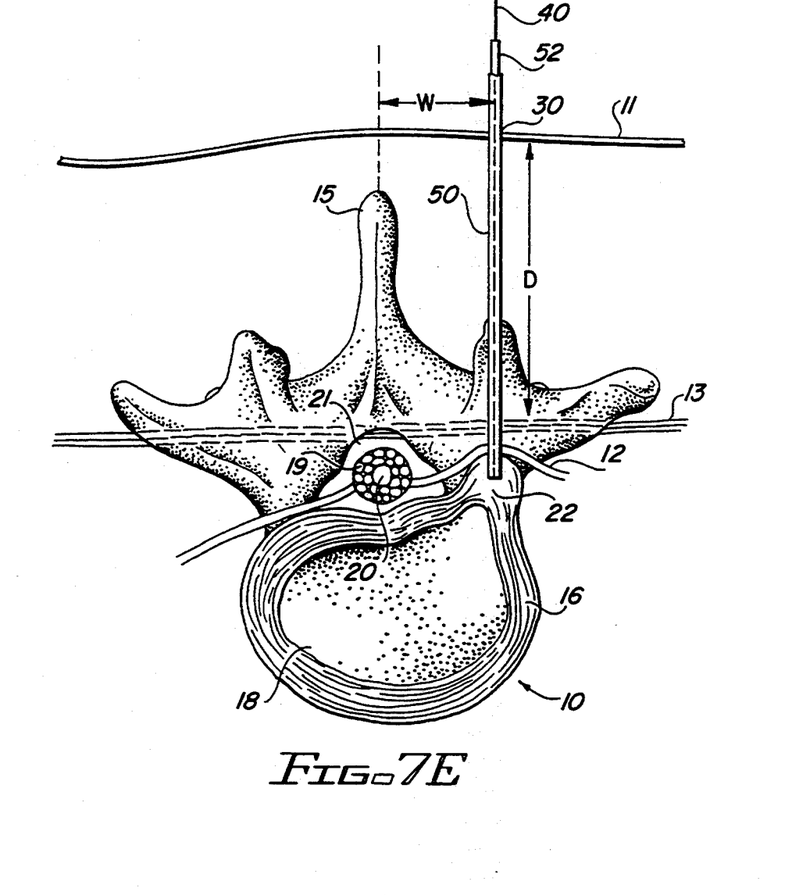
FIG. 7E is a sectional view of a non-contained herniated lumbar disc illustrating insertion of the dilatator in place of the trepan with the dilatator and cannula inserted through the ligamentum flavum.
Figure 8C:
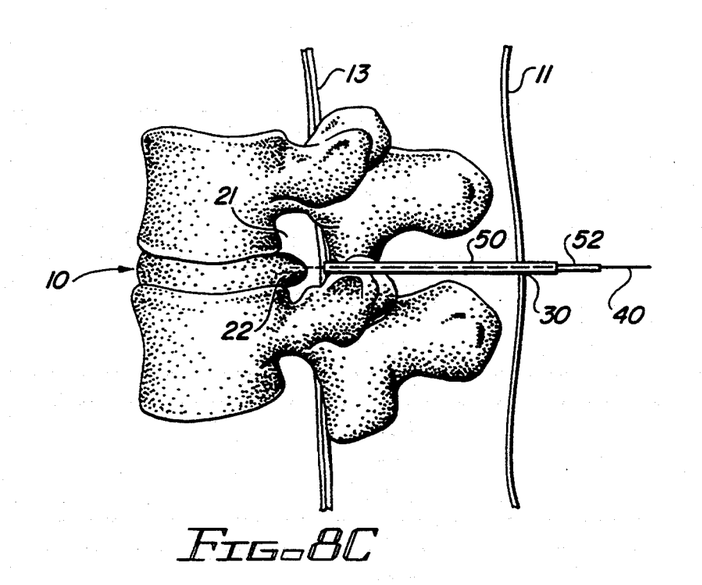
FIG. 8C is an oblique view of a non-contained herniated lumbar disc illustrating insertion of the dilatator and cannula over the leading wire.
Figure 8D:
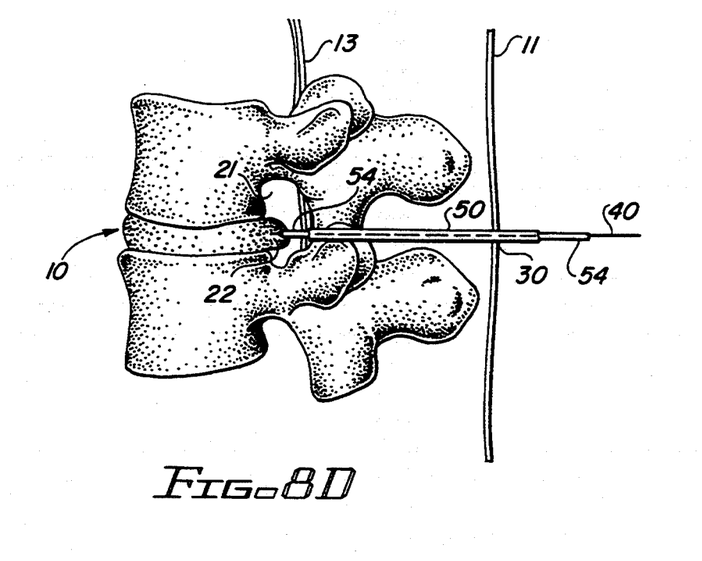
FIG. 8D is an oblique view of a non-contained herniated lumbar disc illustrating insertion of the trepan in place of the dilatator drilling through the ligamentum flavum.
Figure 8E:
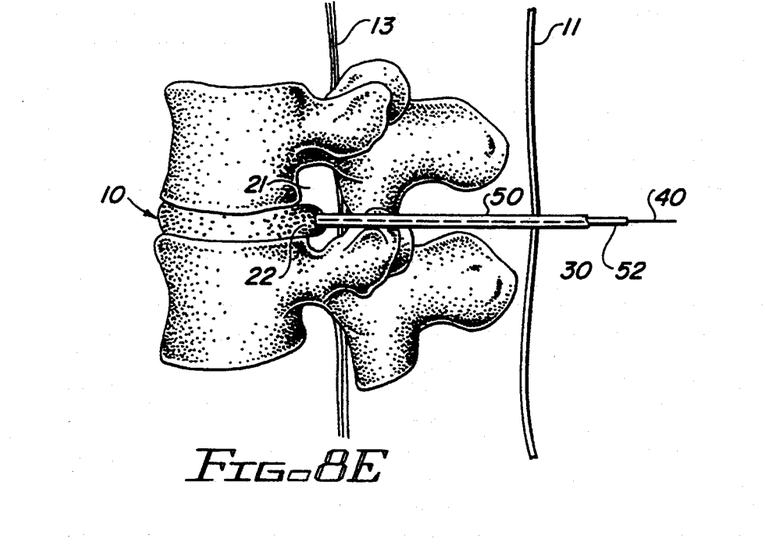
FIG. 8E is an oblique view of a non-contained herniated lumbar disc illustrating insertion of the dilatator in place of the trepan with the dilatator and cannula inserted through the ligamentum flavum.

A cannula 50, FIGS. 7C, 8C and FIG. 9, preferably having a 2.3 mm inner diameter and connection for suction, and a dilatator 52 with a blunt tip, preferably having an inner diameter of 1.5 mm and an outer diameter of 1.8 mm, which is positioned between the leading wire 40 and the cannula 50, are passed over the leading wire 40 down to the ligamentum flavum 13. The position is controlled by the CT. The dilatator 52 is then removed and replaced with a sharp tipped trepan 54 FIGS. 7D and 8D to drill a hole into the ligamentum flavum 13, shown in FIG. 10. Once the ligamentum flavum 13 is passed, the trepan 54 is removed and the dilatator 52 is re-inserted, FIGS. 7E and 8E. The cannula 50 and dilatator 52 are inserted passed the ligamentum flavum 13 and enter the spinal canal 21.

Figure 7F:
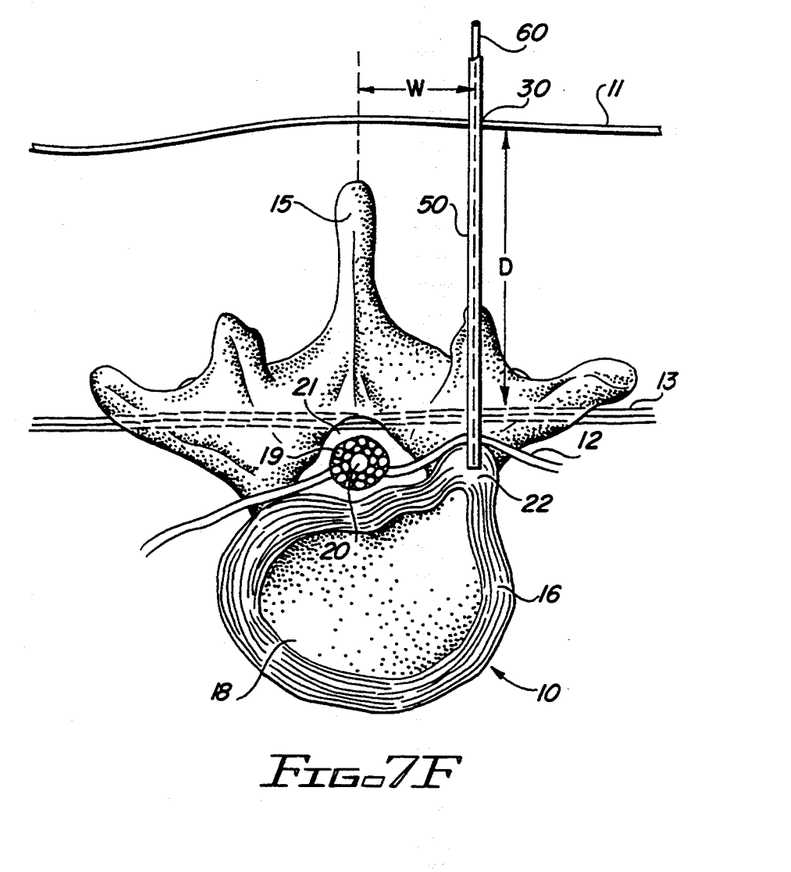
FIG. 7F is a sectional view of a non-contained herniated lumbar disc illustrating insertion of the optical system in place of the leading wire and dilatator.
Figure 8F:
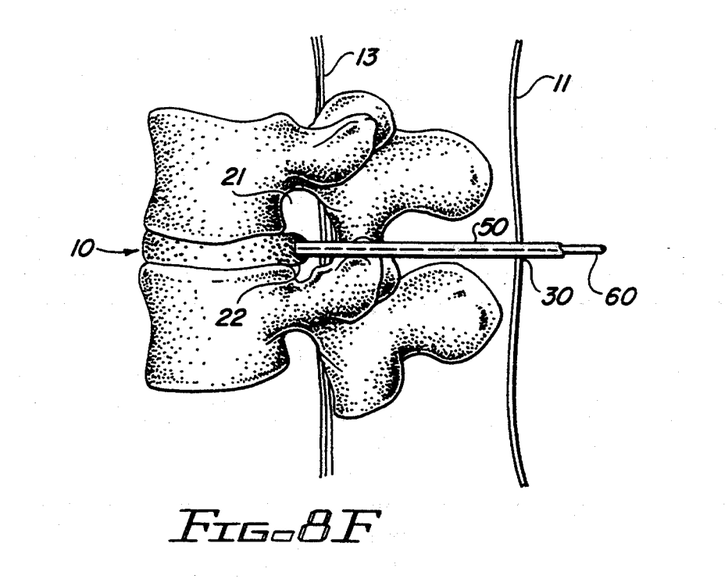
FIG. 8F is an oblique view of a non-contained herniated lumbar disc illustrating insertion of the optical system in place of the leading wire and dilatator.

Referring now to FIGS. 7F, 8F FIG. 11, the dilatator 52 and leading wire 40 can now be removed and replaced with an optical system 60 having a flexible scope 66 with a total diameter of approximately 2.3 mm which includes a laser fiber 62 and illumination 64. The preferred optical system 60 is the "LASE Kit" manufactured by Clarus Medical Systems, Inc. and incorporated herein by reference, shown in FIG. 11.

The prolapsed material 22 may be visualized as well as the spinal cord 20, thecal sac 19, and nerve root 12. Once the prolapse material 22 is identified, the prolapse material 22 is then touched by a laser fiber 62 of the laser optical system 60. Preferably, the laser 62 is applied with low power at first, increasing to a higher power, approximately 15 watts. Applying the laser beam directly in contact with the prolapsed nucleus pulposus material 22, eliminates the prolapsed nucleus pulposus material 22. Once vaporized, the procedure is substantially completed. The final state can verified by the CT. The instruments are then removed and the area closed.

Figure 7G:
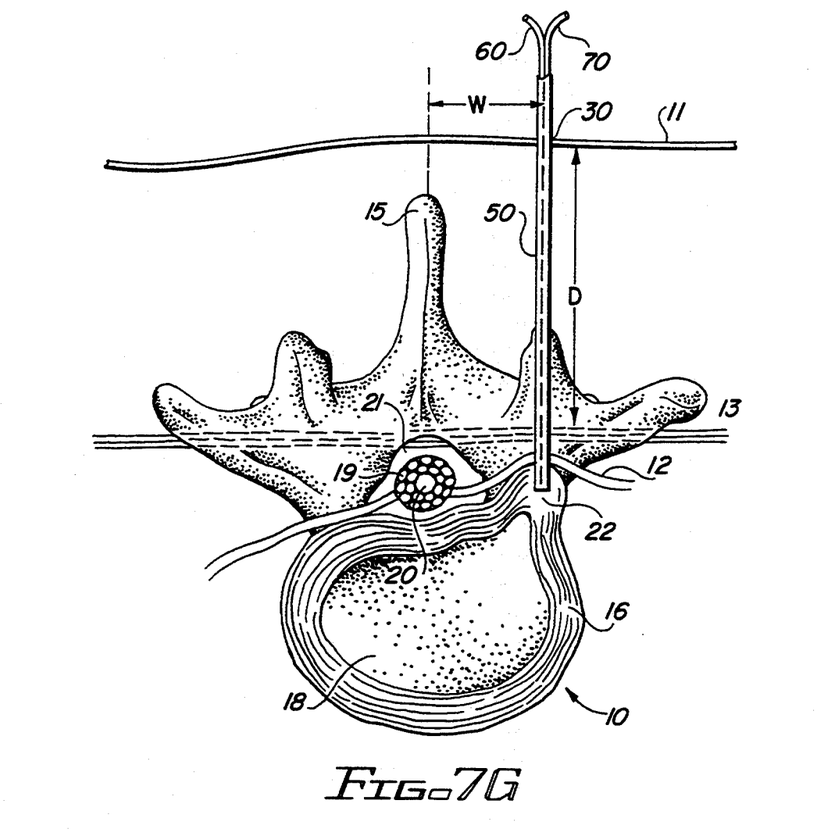
FIG. 7G is a sectional view of a non-contained herniated lumbar disc illustrating insertion of the free channel for suction.
Figure 7H:
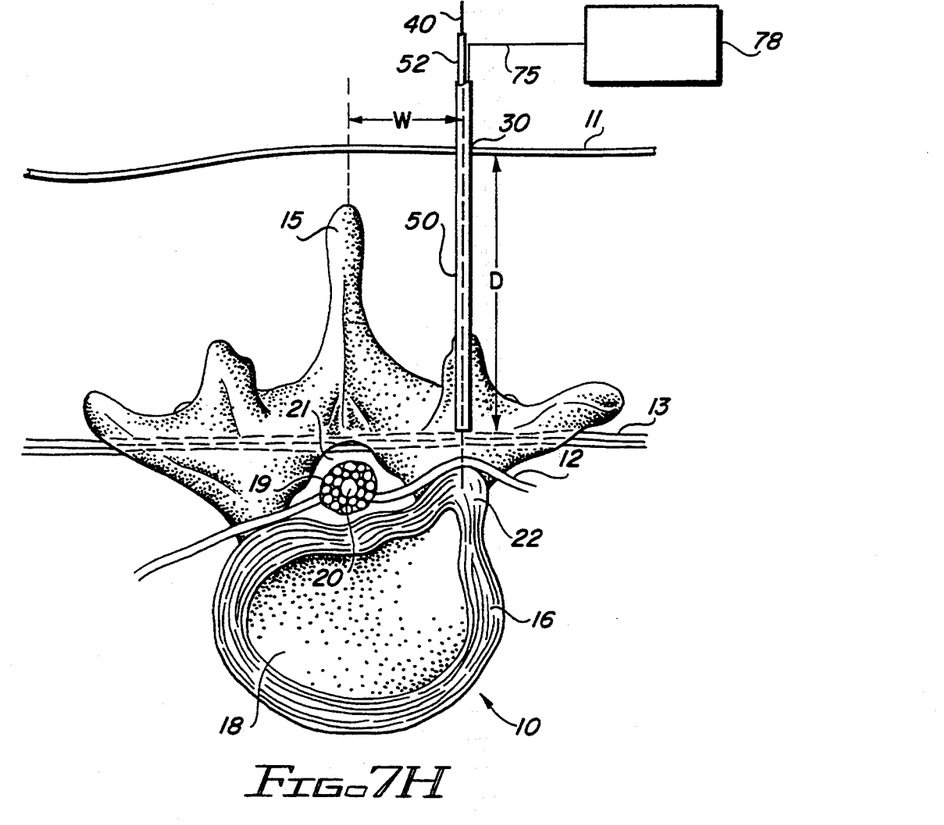
FIG. 7H is a sectional view of a non-contained herniated lumbar disc illustrating insertion of a visual system.
Figure 8G:
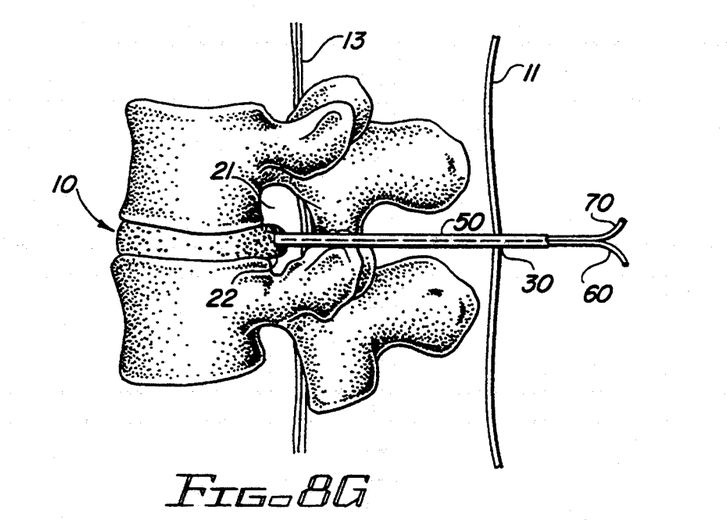
FIG. 8G is an oblique view of a non-contained herniated lumbar disc illustrating insertion of the free channel for suction.
Figure 8H:
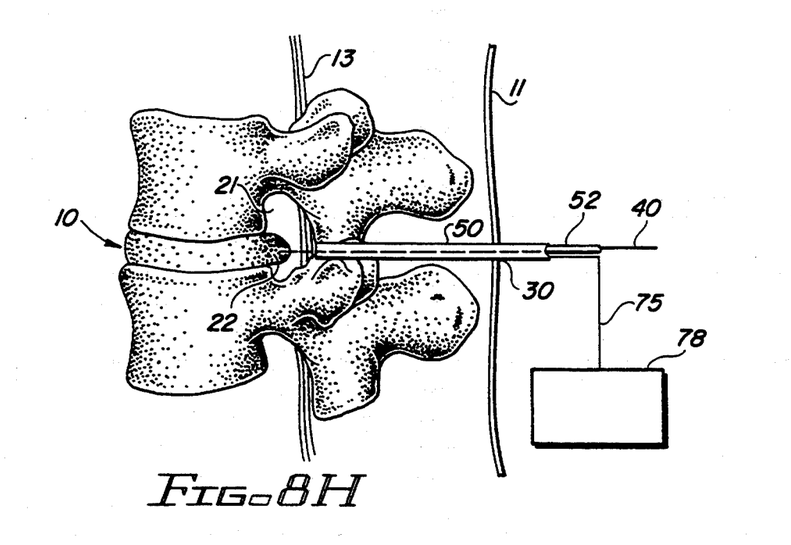
FIG. 8H is an oblique view of a non-contained herniated lumbar disc illustrating insertion of a visual system.

In an alternative embodiment of the invention, the method further comprises prior to the step of puncturing the spinal foramen, employing a visual system 75, FIGS. 7H and 8H throughout to allow visualization of the method. The visual system comprises a fluoroscopic X-ray system, a Computed Tomograph (CT), or a (MRI) Magnetic Resonance Imaging system 78.

In an alternative embodiment of the invention, the method further comprises after the step of inserting a laser fiber 62, inserting a free channel 70, FIGS. 7G and 8G into the spinal foramen 21 for suction.

In an alternative embodiment of the invention, the method further comprises after the step of inserting a laser fiber 62, inserting a second channel, into the spinal foramen 21 for a peristaltic pump, used and well known by those in the medical arts.

In an alternative embodiment of the invention, the method further comprises after the step of passing leading wire 40 through a section of ligamentum flavum 13, cooling an area around the intervertebral disc 10, whereby the cooling extends to an associated root 12 and a section of a spinal cord 20 near the intervertebral disc 10. Any suitable cooling means may be used.

In an alternative embodiment of the invention, the visual system, includes a computer for enhanced visual monitoring.

Accordingly, it will be understood that the preferred embodiment and alternative embodiment of the present invention have been disclosed by way of example and that other modifications and alterations may occur to those skilled in the art without departing from the scope and spirit of the appended claims.

What is claimed is:

1. A method for removal of prolapsed nucleus pulposus material within a spinal foramen of an intervertebral disc of a patient using a laser, comprising the steps of:
- puncturing said patient's skin at an entry point with a leading wire;
- inserting said leading wire into said spinal foramen up to said nucleus pulposus material along an entry path, whereby said entry path passes through a section of ligamentum flavum alongside the dural sac;
- inserting a blunt tipped dilatator and a cannula over said leading wire down to the ligamentum flavum, wherein said dilatator is located between said leading wire and said cannula;
- replacing said dilatator with a sharp tipped trepan;
- drilling a hole through the ligamentum flavum;
- replacing said trepan with said dilatator;
- passing said cannula and said dilatator through said ligamentum flavum into said spinal foramen
- removing said dilatator;
- removing said leading wire from said cannula:
- inserting into said cannula, in place of said leading wire, a laser fiber;
- touching said prolapsed nucleus pulposus material with said laser fiber; and
- applying a laser beam to said prolapsed nucleus pulposus material with said laser fiber,
- whereby said prolapsed nucleus pulposus material is thereafter substantially eliminated.

2. The method of claim 1 further comprising prior to said step of inserting a laser fiber, inserting an optical system into said cannula.

3. The method of claim 1 further comprising prior to said step of puncturing said spinal foramen, employing a visual system throughout to allow visualization of said method.

4. The method of claim 3 wherein said step of employing a visual system comprises employing a fluoroscopic X-ray system.

5. The method of claim 3 wherein said step of employing a visual system comprises employing a Computed Tomograph (CT).

6. The method of claim 3 wherein said step of employing a visual system comprises employing a (MRI) Magnetic Resonance Imaging system.

7. The method of claim 1 further comprising after said step of inserting a laser fiber, inserting a free channel into said spinal foramen for suction.

8. The method of claim 1 further comprising after said step of inserting a laser fiber, inserting a second channel, into said spinal foramen for a peristaltic pump.

9. The method of claim 1 further comprising after said step of passing said leading wire through a section of ligamentum flavum, cooling an area around said intervertebral disc, whereby said cooling extends to an associated root and a section of a spinal cord near said intervertebral disc.

10. The method of claim 3 further comprising prior to said step of puncturing said spinal foramen employing a computer for enhanced visual monitoring.

11. A method for removal of prolapsed nucleus pulposus material within a spinal foramen of an intervertebral disc of a patient using a laser, comprising applying a laser beam directly in contact with said prolapsed nucleus pulposus material, whereby said laser beam eliminates said prolapsed nucleus pulposus material; wherein said step of applying said laser beam comprises the steps of:
- puncturing said patient's skin at an entry point with a leading wire;
- inserting said leading wire into said spinal foramen up to said nucleus pulposus material along an entry path, whereby said entry path passes through a section of ligamentum flavum alongside the dural sac;
- inserting a blunt tipped dilatator and said cannula over said leading wire down to the ligamentum flavum, wherein said dilatator is located between said leading wire and said cannula;
- replacing said dilatator with a sharp tipped trepan;
- drilling a hole through the ligamentum flavum;
- replacing said trepan with said dilatator;
- passing said cannula and said dilatator through said ligamentum flavum into said spinal foramen;
- removing said dilatator from said cannula;
- removing said leading wire from said cannula;
- inserting into said cannula, in place of said leading wire, an optical system into said cannula, wherein said optical system includes a laser fiber;
- touching said prolapsed nucleus pulposus material with said laser fiber; and
- applying a laser beam to said prolapsed nucleus pulposus material with said laser fiber, whereby said prolapsed nucleus pulposus material is thereafter substantially eliminated.

* * * * *